(12) United States Patent
Graham et al.

(10) Patent No.: US 7,022,269 B2
(45) Date of Patent: *Apr. 4, 2006

(54) ACTIVATED CARBON FOR ODOR CONTROL AND METHOD FOR MAKING SAME

(75) Inventors: James Richard Graham, Fountain Valley, CA (US); Cheng Jian Yuan, Ningxia (CN)

(73) Assignee: USFilter Corporation, Warrendale, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/008,449

(22) Filed: Dec. 9, 2004

(65) Prior Publication Data

US 2005/0100491 A1    May 12, 2005

Related U.S. Application Data

(62) Division of application No. 10/014,848, filed on Dec. 11, 2001, now Pat. No. 6,858,192.

(60) Provisional application No. 60/254,900, filed on Dec. 11, 2000.

(51) Int. Cl.
C01B 31/08    (2006.01)
C01B 31/10    (2006.01)

(52) U.S. Cl. .................................... 264/29.1
(58) Field of Classification Search ............. 264/140, 264/29.1, 211.11, 44; 502/182, 183, 185
See application file for complete search history.

(56) References Cited

U.S. PATENT DOCUMENTS

| | | |
|---|---|---|
| 2,822,304 A | 2/1958 | Gillmore et al. |
| 3,416,293 A | 12/1968 | Alexander |
| 3,817,874 A | 6/1974 | Wennerberg et al. |
| 4,008,174 A | 2/1977 | Jacobson et al. |
| 4,125,482 A | 11/1978 | Sinha |
| 4,242,226 A | 12/1980 | Siren |
| 4,252,571 A | 2/1981 | Reilly |
| 4,447,665 A | 5/1984 | Wennerberg |
| 4,482,641 A | 11/1984 | Wennerberg |
| 4,518,488 A * | 5/1985 | Wennerberg ............ 208/216 R |
| 4,831,003 A | 5/1989 | Lang et al. |
| 4,938,046 A | 7/1990 | Kodama et al. |
| 4,970,189 A | 11/1990 | Tachibana |
| 4,978,650 A | 12/1990 | Coughlin et al. |
| 5,037,791 A | 8/1991 | Comolli et al. |
| 5,260,047 A | 11/1993 | Berger |
| 5,356,849 A | 10/1994 | Matviya et al. |
| 5,480,860 A | 1/1996 | Dillon |
| 5,486,356 A | 1/1996 | Yim |
| 5,488,023 A | 1/1996 | Gadkaree et al. |
| 5,492,882 A | 2/1996 | Doughty et al. |
| 5,494,869 A | 2/1996 | Hayden et al. |
| 5,598,868 A | 2/1997 | Jakob et al. |
| 5,948,398 A | 9/1999 | Hanamoto et al. |
| 5,997,829 A | 12/1999 | Sekine et al. |
| 6,010,666 A | 1/2000 | Kurokawa et al. |
| 6,858,192 B1 * | 2/2005 | Graham et al. ............ 423/210 |

FOREIGN PATENT DOCUMENTS

| | | |
|---|---|---|
| EP | 0643014 A1 | 3/1995 |
| EP | 0747118 A2 | 12/1996 |
| FR | 2389381 A1 | 12/1978 |
| JP | 7-313867  * | 5/1995 |
| JP | 7313867 A2 | 12/1995 |
| JP | 9192485 A2 | 7/1997 |

OTHER PUBLICATIONS

Japanese Abstract for No. 2078433A, Dainichiseika Color & Chemical Mfg.; Mar. 19, 1990.
Japanese Abstract for No. 9192485A, Kuraray Chemical Co., LTD.; Jul. 29, 1997.
Japanese Abstract for No. 7313867A, Matushita Electric Works LTD.; Dec. 5, 1995.
International Search Report PCT/US 01/47641; dated Jul. 11, 2002.
Calgon Carbon Corporation, Type Cane CAL Granular Carbon, Bulletin 23-76a, 1987, no month.
Soo-Jin Park and Woo-Young Jung, Influence of Activation Temperature on Micro-and Mesoporosity of Synthetic Activated Carbons, vol. 2, Jun. 2001, pp. 105-108.
Webster's New Collegiate Dictionary (1979), G.&C. Merriam Company, pp. 404, 632, 1979, no month.
International Search Report, PCT/US 03/38504, dated Oct. 20, 2004.

* cited by examiner

Primary Examiner—Wayne A. Langel

(57) ABSTRACT

An activated carbon-metal oxide matrix is disclosed. The activated carbon-metal oxide matrix may by obtained by a method including the steps of: preoxidizing a carbon material, grinding the preoxidized carbon material; mixing the ground preoxidized material with a metal oxide to form a carbon mixture; extruding the carbon mixture; carbonizing and activating the extrudate. The activated carbon-metal oxide matrix may be used to remove odorous compounds, acidic gases, and volatile organic compounds from a gas.

33 Claims, No Drawings

ACTIVATED CARBON FOR ODOR CONTROL AND METHOD FOR MAKING SAME

This application is a divisional application under 35 U.S.C. 120 and claims the benefit of priority to U.S. patent application Ser. No. 10/014,848, filed on Dec. 11, 2001, entitled Activated Carbon for Odor Control and Method for Making Same, U.S. Pat. No. 6,858,192, which is incorporated herein by reference for all purposes, which claims priority to U.S. Provisional Application Ser. No. 60/254,900 filed Dec. 11, 2000 which is incorporated herein by reference for all purposes.

BACKGROUND OF THE INVENTION

1. Field of the Invention

This invention relates generally to an activated carbon for odor control and method for making same, and more particularly, to an activated carbon-metal oxide matrix to control odor in a gaseous stream, and method of making same.

2. Description of the Related Art

Activated carbons have long been known for their capacity to sorb odors. Activated carbons capture substances generally through physical sorption, chemical sorption and catalytic reaction. It is well known that the presence of metals in activated carbon can enhance the efficiency and selectivity of the activated carbon in sorptive or filtering applications. Methods for producing porous structural materials containing adsorbent particles of activated carbon and metals or metal oxides are conventionally known.

Activated carbon impregnated with metals are typically formed by dispersing activated carbon powders in a solution of a metal salt. The powder is filtered out, dried, and heated to decompose the salt to the desired metal or metal oxide catalyst. Multiple impregnations are usually required to obtain the desired quantity of catalyst on the activated carbon.

Another technique for making activated carbon supported catalysts involves depositing a catalyst metal precursor with high vapor pressure onto a carbon surface. Other methods are known to include extruding activated carbon particles with metal or metal oxide particles and a binder.

Siren, in U.S. Pat. No. 4,242,226, discloses an activated carbon matrix filter material having a metal uniformly dispersed therein. The matrix is obtained by chemically reacting cations that comprise the metal with anion groups chemically bound to a polyhexose derivative. The reaction product is separated, pyrolysed and activated.

Tachibana, in U.S. Pat. No. 4,970,189, discloses fine metal particles dispersed in a carbonaceous mixture. The carbonaceous mixture may be obtained by mixing metal oxide particles with an organic substance and carbonizing the mixture in a non-oxidizing atmosphere to convert the organic substance into a porous carbonaceous body and to convert the metal oxide particles into elemental metal particles dispersed in the carbonaceous body. The metal oxide particles may be coated with an anionic surfactant to provide homogeneity in dispersion of the metal oxide in the organic substance.

Gadkaree et al., in U.S. Pat. No. 5,488,023, disclose a method for making an activated carbon supported catalyst comprising combining a carbon precursor and a catalyst precursor, curing the carbon precursor if necessary, carbonizing the carbon precursor, and activating the carbon. The activated carbon supported catalyst can take the form of a coating on a substrate, a powder, or a monolithic body.

Other examples of activated carbons and metal oxides include: U.S. Pat. No. 4,482,641 to Wennerberg; U.S. Pat. No. 4,831,003 to Lang et al.; U.S. Pat. No. 5,948,398 to Hanamoto et al., and U.S. Pat. No. 5,997,829 to Sekine et al.

SUMMARY OF THE INVENTION

In one embodiment, the present invention is directed to an activated carbon matrix having between about 3% and about 15% by weight of a metal oxide uniformly dispersed therein.

Another embodiment is directed to a process for preparing a media for filtering gaseous substances. The process includes preoxidizing a carbon material; grinding the preoxidized carbon; combining the ground preoxidized carbon and a metal oxide to form a carbon mixture; extruding the carbon mixture; and carbonizing and activating the extrudate.

Another embodiment is directed to a method of forming an activated carbon-metal oxide matrix including: preoxidizing a carbon material; grinding the preoxidized carbon to form a ground carbon; combining the powder, coal tar pitch, and the metal oxide to from a paste; extruding the paste; and carbonizing and activating the extrudate.

Another embodiment is directed to a method for removing odors from a gaseous stream comprising: forming an activated carbon-metal oxide matrix, wherein the matrix has a hydrogen sulfide breakthrough capacity greater than about 0.3 g$H_2$S/ccC; contacting the stream with the matrix; sorbing the odorous compound on the matrix; and removing the stream from the matrix.

Another embodiment is directed to a method for reducing concentrations of odorous compounds in a gaseous stream including: contacting the gaseous stream with an activated carbon material comprising about 3% to about 15% of a metal oxide; sorbing the odorous compounds on the activated carbon material to produce a product stream; and removing the product stream from the activated carbon material.

Another embodiment is directed to a method for reducing a concentration of sulfides present in a gaseous discharge from a waste water treatment system including: providing a gaseous discharge including a volatile organic compound and a sulfide; contacting the gaseous discharge with an activated carbon-metal oxide matrix; sorbing the sulfide on the matrix to produce a product stream having a sulfide concentration less than about 0.1 ppm; and removing the product stream from the activated carbon-metal oxide matrix.

Another embodiment discloses a metal oxide-carrying activated carbon for removing hydrogen sulfide from a gas including an activated carbon-metal oxide matrix obtained by mixing about 3% to about 15% by weight of a metal oxide; carbonizing and activating the matrix.

DETAILED DESCRIPTION

The present invention provides an activated carbon-metal oxide matrix and methods of making and using same. Activated carbon is a porous material characterized by a high carbon content and a large surface area, and is typically a mixture of amorphous carbon and graphite crystals, rather than an homogeneous, well defined material. The term "activated carbon" generally refers to a black, solid carbonaceous material, such as charcoal, bone charcoal, sugar charcoal, carbon produced from oil products, coconut carbon, and the like, that remains after the decomposition of organic material by pyrolysis, and undergoes an activating process, during or after the pyrolysis. Activation is typically done by known methods such as exposing the structure to an oxidizing agent such as steam, carbon dioxide, metal chloride (e.g., zinc chloride), phosphoric acid, or potassium sulfide, at high temperatures. Temperatures sufficient for activation generally range from about 800° C. to about 1000° C. (1450° F. to 1850° F.). Activation creates a high surface area and in turn imparts high adsorptive capability to the structure.

The activated carbon-metal oxide matrix according to the present invention, may be prepared, in general, by preoxidizing a carbon material; grinding the preoxidized carbon material; combining the ground preoxidized carbon material with a metal oxide to form a carbon mixture; extruding the carbon mixture to form an extrudate; carbonizing the extrudate to form a carbonaceous mixture; and activating the carbonaceous mixture. The term "matrix" is defined as that which gives origin or form to a thing or which serves to enclose it. As used herein, the phrase "activated carbon-metal oxide matrix" refers to an activated carbon matrix having a metal oxide uniformly dispersed therein.

Any carbon material may be used in the present invention, so long as it results in a porous carbon material when heated in a non oxidizing condition. For example, carbon materials usable in the present invention include: charcoal, coconut shell, bone charcoal, sugar charcoal, coal and other conventional carbon materials. The carbon material may by crushed prior to preoxidation. The carbon material may be ground to a powder. As used herein, the term "powder" is defined as a loose grouping or aggregation of solid particles having a diameter smaller than about 1 mm. Alternatively, the carbon may be ground to granules. As used herein, the term "granule" is defined as a loose grouping or aggregation of solid particles having a diameter from about 1 mm to about 4 mm. In a preferred embodiment, the carbon material is ground to a granular size of about 1 mm to about 2 mm. The ground carbon material is subjected to preoxidation in air at a low temperature, for example about 600° F.

Any metal oxide that enhances the sorptive capacity of activated carbons may be used in the present invention. As used herein, the term "sorb" is defined as the capture of substances generally through physical sorption, chemical sorption and catalytic reaction. Metal oxides usable in the present invention include metal oxides selected from the group consisting of the oxides of Ca, Mg, Ba, Be, Sr, Sc, Y, La, Lanthanide Series, Ti, Zr, Hf, V, Nb, Ta, Cr, Mo, W, Mn, Fe, Co, Ni, Cu, Zn, and combinations thereof. In one embodiment, the metal oxide is selected from the oxides of Mg, Ca, and Ba. In a preferred embodiment, the metal oxide is magnesium oxide. The metal oxide may be in any form, such as, for example, granules or powder. The metal oxide in powder form may be of any size and have any size distribution. In a preferred embodiment, the metal oxide powder is about 325 mesh, and more preferably about 200 mesh or finer.

The carbon material and metal oxide are mixed to form a carbon mixture. Generally, about 3% to about 15% by weight of the metal oxide is mixed with the carbon material. In one embodiment, about 5% to about 10% by weight of the metal oxide is mixed with the carbon material. In a preferred embodiment, the carbon mixture comprises about 5% by weight of the metal oxide.

In one embodiment, the carbon material and the metal oxide may be mixed in the presence of a binder and, if necessary, a solvent, as is know in the art to form an extrudable paste. In another embodiment, the carbon material and the metal oxide may be combined to form a carbon mixture and further ground to a powder before being mixed in the presence of a binder and, if necessary, a solvent to form the extrudable paste. The carbon mixture may be ground in a pendulum type-4 ring roll pulverizer utilizing centrifugal force to pass the carbon mixture through a mesh, as is know in the art. In a preferred embodiment, the carbon mixture is ground and, if necessary, reground so that approximately 95% of the carbon mixture passes through a 200 mesh.

The binder may be any known material capable of forming a paste with the carbon material and metal oxide. For example, the binder may be molasses, avicel, soft pitch, coal tar, coal tar pitch, and combinations thereof. In a preferred embodiment, the binder is about 40% coal tar and about 60% coal tar pitch. The solvent may be any suitable liquid capable of forming an extrudable paste with the carbon material, metal oxide, and binder. For example, the solvent may be water or an organic solvent. In a preferred embodiment, the solvent is water.

The carbon mixture is extruded to form an extrudate capable of being carbonized. Extruders, such as high pressure hydraulic extruders, are known in the art. The extrudate may be of any suitable shape, such as, for example, strands and ribbons. In a preferred embodiment, the carbon mixture is extruded into strands, about 6 mm to about 8 mm long, having a diameter of about 4 mm. In one embodiment, the extruded carbon mixture is re-extruded prior to further processing. The extrudate may be allowed to cool to ambient temperature.

The extrudate is carbonized at a temperature and a period of time sufficient to convert the carbon material into a porous carbonaceous mixture. Carbonization is generally performed in the absence of air at a temperature of about 1000° F. If desired, the carbonaceous mixture may also be crushed to yield a fine granular product. The carbonaceous mixture is then activated according to known procedures, for example, in the presence of steam at about 1600° F. to about 1700° F. If desired, the activated carbonaceous mixture may be further treated to obtain the desired physical characteristics. For example, the finished product may be screened according to particle size distribution.

Although not being limited to any particular theory, it is believed that the metal oxide is highly dispersed throughout the activated carbon and therefore, does not occupy and reduce the overall pore volume of the activated carbon. Moreover, addition of the metal oxide in the described manner apparently increases the macroporosity and total pore volume of the activated carbon.

The activated carbon-metal oxide matrix may be used to sorb odors from a wide variety of sources, including: municipal, industrial and residential sources. For example, the activated carbon-metal oxide matrix of the invention is suitable for sorbing odorous compounds typical of chemical processes found in sewage treatment plants, refineries, and pulp and paper mills. The activated carbon-metal oxide matrix may also be used to remove odorous compounds from a gas or gaseous stream containing volatile organic compounds, such as, for example aldehydes and ketones, and/or acidic gasses such as, for example, butyric acid, hydrogen chloride and sulfur dioxide.

Typical gases that may be purified by contact with the activated carbon-metal oxide matrix include, but are not limited to, air, nitrogen and carbon dioxide. Moisture may also be present in the gas so long as it does not condense on the activated carbon-metal oxide matrix. In one embodiment, the gas has a moisture content of about 60% to about 95% RH. The gas to be purified may also contain oxygen.

For example, the activated carbon-metal oxide matrix of the invention typically oxidizes hydrogen sulfide in the following exothermic reaction.

$$2H_2S + O_2 \rightarrow 2H_2O + 2S$$

The activated carbon/metal oxide matrix reduces hydrogen sulfide concentrations to below odor threshold levels by catalyticaly oxidizing the hydrogen sulfide to elemental sulfur.

Typical industrial uses may include packing a bed or column with the activated carbon-metal oxide matrix of the present invention. For example, packed beds used in sewage treatment facilities range from about 3 feet to about 12 feet in diameter, and about 4 feet to about 6 feet in depth with a typical gas velocity through the bed or about 20 fpm to about 80 fpm. In a preferred embodiment, the gas velocity is about 60 fpm. The activated carbon-metal oxide packed bed may be operated at any pressure to meet throughput and at any temperature below the ignition temperature of carbon.

Sewage treatment plants produce sewage gas containing hydrogen sulfide and other organic sulfides that cause it to be malodorous. In addition, most chemical compounds that cause odors in sewage gas are toxic and corrosive. Examples of sulfur-containing substances known to cause the odor in sewage gas, are, allyl mercaptan, amyl mercaptan, benzyl mercaptan, croytl mercaptan, dimethyl sulfide, ethyl mercaptan, hydrogen sulfide, and sulfur dioxide, among others. The activated carbon-metal oxide matrix efficiently oxidizes mercaptans to their respective disulfides making them more adsorbable.

Hydrogen sulfide, generally the major component of sewage gas, present at relatively high concentrations, is used as a measure of the odor intensity and corrosiveness of sewage gas. In addition to causing an intense odor associated with rotten eggs, hydrogen sulfide may be quite hazardous, causing physiological effects. A hydrogen sulfide concentration of about 0.1 ppm of sewage gas can be detected by the human nose, which although unpleasant, may be relatively harmless. However, as the concentration of hydrogen sulfide increases, various physical effects to exposure may be, for example, headache, nausea, and throat and eye irritation. At a hydrogen sulfide concentration of about 500 ppm of sewage gas, life threatening effects will occur, such as pulmonary edema, nervous system stimulation and apnea. Exposure to a hydrogen sulfide concentration of about 1,000 ppm to about 2,000 ppm of sewage gas may result in respiratory collapse, paralysis, and death.

The ability of an activated carbon to sorb hydrogen sulfide is reported in grams of hydrogen sulfide adsorbed per cubic centimeter of carbon, also known as the hydrogen sulfide breakthrough capacity. The hydrogen sulfide breakthrough capacity is determined by passing a moist (about 85% RH) stream of air containing 1 vol. % hydrogen sulfide through a one-inch diameter tube with a 9-inch deep bed of closely packed carbon at a rate of 1450 cc/min. The stream is monitored to a 50 ppmv hydrogen sulfide breakthrough. The activated carbon-metal oxide matrix has a minimum hydrogen sulfide breakthrough capacity of about 0.3 gH$_2$S/ccC as illustrated in the following Examples.

EXAMPLES

The invention may be further understood with reference to the following examples, which are intended to serve as illustrations only, and not as limitations of the present invention as defined in the claims herein.

Example I

The activated carbon-metal oxide matrix was formed by first crushing bituminous coal and preoxidizing the coal in air at approximately 600° F. The preoxidized coal was ground to a powder and mixed with about 6% magnesium oxide powder. The carbon mixture of preoxidized coal and magnesium oxide was mixed with coal tar pitch and water; extruded into typically 4 mm diameter strands; and carbonized in the absence of air at about 1000° F. The carbonaceous mixture was activated in the presence of steam at about 1700° F. The resulting activated carbon-metal oxide matrix was tested for hydrogen sulfide breakthrough. In separate tests, the activated carbon-metal oxide matrix has a hydrogen sulfide breakthrough capacity of: 0.30, 0.46, 0.54, and 0.65 gH$_2$S/ccC, respectively.

The hydrogen sulfide breakthrough capacity was also determined for several commercially available activated carbons. One such carbon, UOCH-KP® activated carbon impregnated with KOH, available from U.S. Filter Corporation (Los Angeles, Calif.) has a hydrogen sulfide breakthrough capacity of 0.14, 0.18, and 0.17 in separate tests. Similarly, UOCH-KP® type carbon impregnated with NaOH instead of KOH, also available from U.S. Filter Corporation, has a hydrogen sulfide breakthrough capacity of 0.18 gH$_2$S/ccC. Another such carbon, Centaur® 4×6, available from Calgon Carbon Corporation (Pittsburgh, Pa.), has a hydrogen sulfide breakthrough capacity of 0.09 gH$_2$S/ccC.

The activated carbon-metal oxide matrix of the invention has a hydrogen sulfide breakthrough capacity 3–5.4 times that of commercially available impregnated activated carbons. Because the activated carbon-metal oxide matrix has a greater capacity to sorb hydrogen sulfide than commercially available impregnated activated carbons, filter beds comprising the activated carbon-metal oxide matrix may be changed less frequently. Moreover, the activated carbon-metal oxide matrix effectively oxidizes hydrogen sulfide to elemental sulfur with minimal conversion to sulfate (sulfuric acid). Because of this, the pH of the matrix does not change significantly with use. Therefore, spent activated carbon-metal oxide matrix is safer to handle than spent impregnated activated carbons, that typically become very acidic. In addition, the activated carbon-metal oxide matrix has an ignition temperature similar to that for virgin activated carbons, i.e. about 450° C. (842° F.), in contrast to the low ignition temperature associated with impregnated activated carbons, i.e. about 150° C. (302° F.). As a result, the activated carbon-metal oxide matrix is safer to handle than the impregnated activated carbon.

Example II

An activated carbon-metal oxide matrix was formed according to the process of Example I. The hydrogen sulfide breakthrough capacity of the activated carbon-metal oxide matrix measured in a gas stream fully saturated with xylene was 0.26 gH$_2$S/ccC. The hydrogen sulfide breakthrough capacity of UOCH-KP® carbon in a gas stream fully saturated with xylene was 0.04 gH$_2$S/ccC. Presence of xylene in the stream reduces the average hydrogen sulfide breakthrough capacity of the impregnated carbon by approximately 75%, and of the matrix by approximately 47%. The matrix is, therefore, less sensitive to organics in a stream than commercially available impregnated activated carbons.

The above description and examples are meant to be taken as exemplary only, of preferred embodiments of the invention. As such, the invention can be practiced according to other techniques and equivalents thereof.

What is claimed is:

1. A process for preparing a media for filtering gaseous substances, comprising:
   preoxidizing a carbon material to form preoxidized carbon;
   grinding the preoxidized carbon;
   combining the ground preoxidized carbon and a metal oxide to form a carbon mixture;
   extruding the carbon mixture to form an extrudate;
   carbonizing the extrudate to form a porous carbonaceous mixture; and
   activating the porous carbonaceous mixture.

2. The process of claim 1, wherein grinding the preoxidized carbon forms granules.

3. The process of claim 2, further comprising grinding the carbon mixture prior to extruding the carbon mixture.

4. The process of claim 3, wherein the carbon mixture is combined with a binder prior to extruding the carbon mixture.

5. The process of claim 4, wherein the carbon mixture and binder is combined with a solvent prior to extruding the carbon mixture.

6. The process of claim 1, wherein grinding the preoxidized carbon forms a powder.

7. The process of claim 6, wherein the ground preoxidized carbon and the metal oxide are combined in the presence of a binder.

8. The process of claim 7, wherein the binder is coal tar pitch.

9. The process of claim 8, wherein the ground preoxidized carbon, the metal oxide, and the coal tar pitch are combined in the presence of water to form a carbon mixture.

10. The process of claim 9, wherein the carbon mixture formed is a paste.

11. The process of claim 1, wherein the coal is peroxidized in air at approximately 600° F.

12. The process of claim 1, wherein a metal oxide at about 3% to about 15% by weight is combined with ground preoxidized carbon.

13. The process of claim 12, wherein a metal oxide at about 5% to about 10% by weight is combined with the ground preoxidized carbon.

14. The process of claim 11, wherein the extrudate is carbonized in the absence of air at approximately 1000° F.

15. The process of claim 14, wherein the carbonaceous mixture is activated with steam between about 1600° F. and about 1700° F.

16. The process of claim 1, further comprising crushing the carbon material before preoxidizing the coal.

17. The process of claim 1, further comprising crushing the carbonaceous mixture prior to activating the carbonaceous mixture.

18. The process of claim 1, wherein the carbon material to be preoxidized is selected from the group consisting of: coconut shell and coal.

19. The process of claim 18, wherein the coal is bituminous low ash coal.

20. The process of claim 1, wherein the metal oxide is selected from the group consisting of the oxides of Ca, Mg, Ba, and combinations thereof.

21. The process of claim 20, wherein the metal oxide is magnesium oxide.

22. A method of forming an activated carbon-metal oxide matrix comprising:
   preoxidizing a carbon material to form a preoxidized carbon;
   grinding the preoxidized carbon to form ground carbon;
   combining the ground carbon, the metal oxide and coal tar pitch to form a paste;
   extruding the paste to form an extrudate;
   carbonizing the extrudate to form a carbonaceous mixture; and
   activating the carbonaceous mixture with steam.

23. The method of claim 22, wherein the ground carbon is a powder.

24. The method of claim 22, wherein the ground carbon is granules.

25. The method of claim 24, wherein the act of combining the ground carbon, metal oxide and coal tar pitch includes grinding metal oxide combined with the ground carbon prior to combining with the coal tar pitch.

26. The method of claim 22, wherein the metal oxide is combined at about 3% to about 15% by weight.

27. The method of claim 26, wherein the metal oxide is combined at about 5% to about 10% by weight.

28. The method of claim 22, wherein the carbon material is preoxidized in air at approximately 600° F.

29. The method of claim 28, wherein the extrudate is carbonized in the absence of air at approximately 1000° F.

30. The method of claim 29, wherein the carbonaceous mixture is activated with steam between about 1600° F. to about 1700° F.

31. The method of claim 22, wherein the carbon material is coal.

32. The method of claim 22, wherein the metal oxide is selected from the group consisting of the oxides of Ca, Mg, Ba, and combinations thereof.

33. The method of claim 32, wherein the metal oxide is magnesium oxide.

* * * * *

UNITED STATES PATENT AND TRADEMARK OFFICE
CERTIFICATE OF CORRECTION

PATENT NO. : 7,022,269 B2  
APPLICATION NO. : 11/008449  
DATED : April 4, 2006  
INVENTOR(S) : James Richard Graham and Jianyuan Cheng It is certified that error appears in the above-identified patent and that said Letters Patent is hereby corrected as shown below:

FROM: (75) Inventors: James Richard Graham, Fountain Valley, GA (US); Cheng Jian Yuan, Ningxia (CN)

TO: (75) Inventors: James Richard Graham, Fountain Valley, CA (US); Jianyuan Cheng, Ningxia (CN)

Signed and Sealed this

Twenty-eighth Day of November, 2006

JON W. DUDAS  
*Director of the United States Patent and Trademark Office*